US00PP33880P2

(12) United States Plant Patent
van Staalduinen

(10) Patent No.: US PP33,880 P2
(45) Date of Patent: Jan. 18, 2022

(54) *EUPHORBIA* PLANT NAMED '16EUPD1'

(50) Latin Name: *Euphorbia hypericifolia*
Varietal Denomination: 16EUPD1

(71) Applicant: Keep Smiling B.V., 's-Gravenzande (NL)

(72) Inventor: Eliza van Staalduinen, 's-Gravenzande (NL)

(73) Assignee: KEEP SMILING B.V., 's-Gravenzande (NL)

( * ) Notice: Subject to any disclaimer, the term of this patent is extended or adjusted under 35 U.S.C. 154(b) by 0 days.

(21) Appl. No.: 17/350,022

(22) Filed: Jun. 17, 2021

(30) Foreign Application Priority Data

Oct. 27, 2020 (QZ) ..... PBR 2020/2438

(51) Int. Cl.
*A01H 5/02* (2018.01)
*A01H 6/38* (2018.01)

(52) U.S. Cl.
USPC ..... Plt./304
CPC ..... *A01H 6/385* (2018.05)

(58) Field of Classification Search
USPC ..... Plt./304
CPC ..... A01H 6/385; A01H 5/02
See application file for complete search history.

*Primary Examiner* — Keith O. Robinson
(74) *Attorney, Agent, or Firm* — Penny J. Aguirre

(57) ABSTRACT

A new cultivar of *Euphorbia* plant named '16EUPD1' that is characterized by its compact, upright, slightly outwardly spreading plant habit, its freely branched growth habit, its free flowering habit, its small dark green leaves, its inflorescenses with a double small flower bracts that are pure white in color, and its high heat tolerance.

2 Drawing Sheets

Botanical classification: *Euphorbia hypericifolia.*
Varietal denomination: '16EUPD1'.

CROSS REFERENCE TO A RELATED APPLICATION

This application is related to a European plant breeders' rights application filed on Oct. 5, 2020, application No. 2020/2438. There have been no offers for sale anywhere in the world prior to the effective filing date of this Application and no accessibility to one of ordinary skill in the art could have been derived from the printed plant breeder's rights documents.

BACKGROUND OF THE INVENTION

The present invention relates to a new and distinct cultivar of *Euphorbia hypericifolia* and will be referred to hereafter by its cultivar name, '16EUPD1'. '16EUPD1' represents a new herbaceous perennial grown for landscape and container use.

The Inventor discovered the new cultivar in May of 2014 as a naturally occurring chimeral mutation of *Euphorbia* 'GL Hip Hop' (U.S. Plant Pat. No. 22,222) in a production field of *Euphorbia* in Worms, Germany.

Asexual propagation of the new cultivar was first accomplished by tissue culture using meristematic tissue under the direction of the Inventor in June of 2018 in Twello, The Netherlands. Asexual propagation by tissue culture and stem cuttings has shown that the characteristics of the new cultivar are stable and are reproduced true to type in successive generations.

SUMMARY OF THE INVENTION

The following traits have been repeatedly observed and represent the characteristics of the new cultivar. These attributes in combination distinguish '16EUPD1' as a new and unique cultivar of *Euphorbia.*

1. '16EUPD1' exhibits a compact, upright, slightly outwardly spreading plant habit.
2. '16EUPD1' exhibits a freely branching growth habit.
3. '16EUPD1' exhibits a free flowering habit.
4. '16EUPD1' exhibits small dark green leaves.
5. '16EUPD1' exhibits inflorescenses with a double small flower bracts that are pure white in color.
6. '16EUPD1' exhibits a high heat tolerance.

The parent plant differs from '16EUPD1' in having single flower bracts and a more vigorous growth habit. '16EUPD1' can also be compared to the *Euphorbia hypericifolia* cultivars 'Silverfrog' (U.S. Plant Pat. No. 20,858) and 'Inneuphdia' (U.S. Plant Pat. No. 17,567). Both 'Silverfrog' and 'Inneuphdia' are similar to '16EUPD1' in having green foliage with flower bracts that are white in color. 'Silverfrog' differs from '16EUPD1' in having a wider plant width and petioles with strong anthocyanin coloration. 'Inneuphdia' differs from '16EUPD1' in having a larger plant size, leaves that is lighter green in color and larger in size, single flower bracts that are less pure white in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosure includes but may not be limited to a website disclosure by Sygenta Flowers.

BRIEF DESCRIPTION OF THE DRAWINGS

The accompanying colored photographs illustrate the overall appearance and distinct characteristics of the new *Euphorbia*. The photographs were taken of a plant 15 weeks in age as grown in a 19-cm container in Andijk, The Netherlands.

The photograph in FIG. 1 provides a side view of a plant of '16EUPD1' in bloom.

Figure 1:
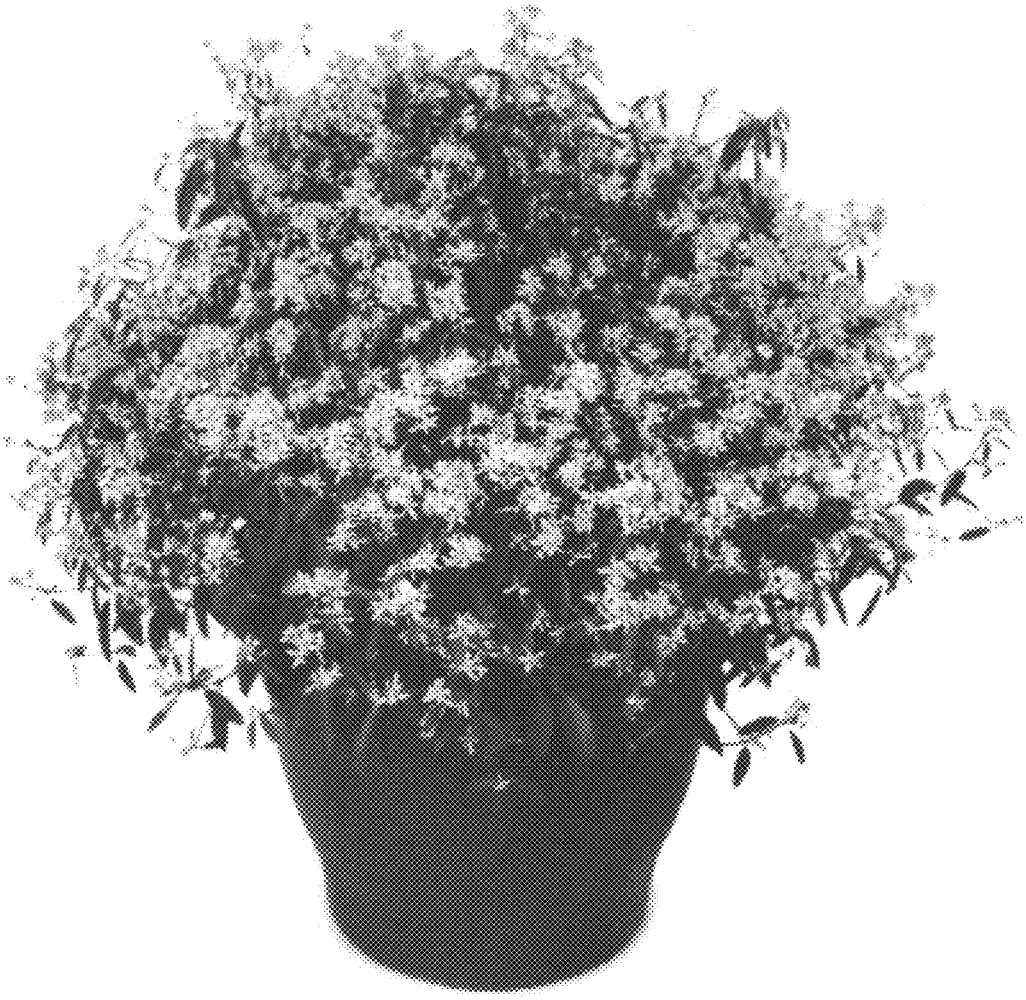
Figure 2:
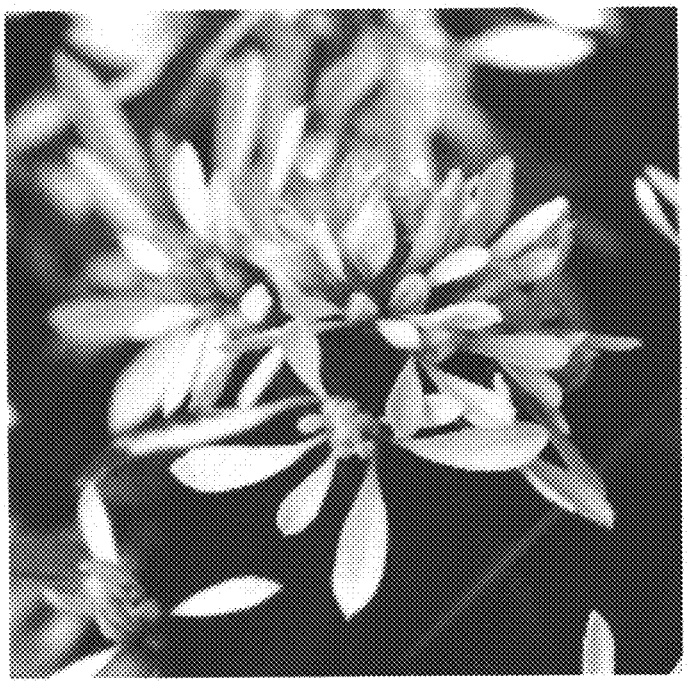

The photograph in FIG. 2 provides a close-up view of an inflorescence of '16EUPD1'.

Figure 3:
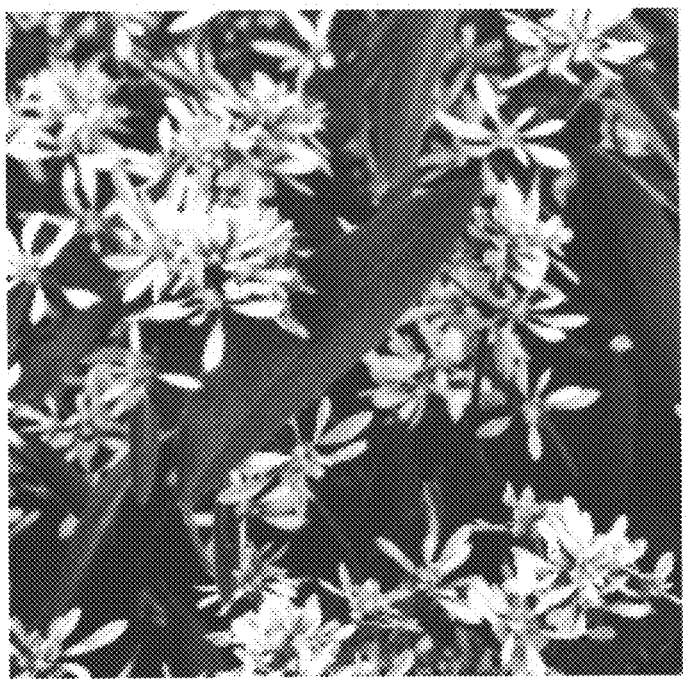

The photograph in FIG. 3 provides a close-up view of the foliage of '16EUPD1'.

The colors in the photographs are as close as possible with the photographic and printing technology utilized and the color values cited in the detailed botanical description accurately describe the colors of the new *Euphorbia*.

DETAILED BOTANICAL DESCRIPTION OF THE PLANT

The following is a detailed description of 18-week-old plants of the new cultivar as grown outdoors in one-quart containers in Gilroy, Calif. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—April through November in The Netherlands.

*Plant type*.—Herbaceous perennial, grown as an annual in cold climates.

*Plant habit*.—Compact, upright, slightly outwardly spreading.

*Height and spread*.—An average of 15 cm in height, 31 cm in width in a one-quart container, mature plant in the landscape reaches an average of 36 cm in height and 48 cm in width.

*Hardiness*.—At least to U.S.D.A. Zones 10 to 11.

*Diseases and pests*.—No susceptibility or resistance to diseases or pests has been been observed.

*Root description*.—Fine, fibrous, 155D in color.

*Root development*.—Average of 12 days to initiate roots (summer), average of 14 days to initiate roots (winter at 22° C.), and a young rooted plant is produced in about 4 weeks from a rooted cutting.

*Propagation type*.—Stem cuttings and tissue culture.

*Growth rate*.—Slow.

Stem description:

*Stem shape*.—Rounded.

*Stem color*.—Young and mature stems; 143A and 142C, sometimes very lightly flushed at with 178A, older bark at base of plant; 174A.

*Stem size*.—Main branches; average of 10 cm in length, 2 mm in width, lateral branches; average of 11 cm in length (including inflorescence) and 1 mm in width.

*Stem surface*.—Slightly glossy, smooth, very sparsely covered with stiff hairs, NN155D in color, 0.5 mm in length.

*Stem aspect*.—Held in various angles, mostly outward from center.

*Stem strength*.—Flexible but strong.

*Internode length*.—An average of 2.5 cm.

*Branching habit*.—Freely branching, 3 main branches, an average of 6 lateral branches per main branch.

Foliage description:

*Leaf shape*.—Elliptic.

*Leaf division*.—Simple.

*Leaf base*.—Acute.

*Leaf apex*.—Bluntly acute.

*Leaf venation*.—Pinnate, not conspicuous.

*Leaf margins*.—Entire and densely covered with minute downy hairs NN155C in color, less than 0.3 mm in length.

*Leaf attachment*.—Petiolate.

*Leaf arrangement*.—Opposite.

*Leaf surface*.—Young and mature upper surface; dull, slightly velvety, soft to the tough, densely covered with tiny downy hairs that match the leaf color and <0.5 mm in length, young and mature lower surface; glabrous, dull.

*Leaf color*.—Upper surface; 137A, lower surface 137C.

*Leaf number*.—Average of 6 per lateral branch.

*Leaf size*.—Up to 3 cm in length and 1 cm in width.

*Petioles*.—Up to 2.5 cm in length and 1.2 mm in width, glabrous surface, 137C in color.

Flower description:

*Inflorescence type*.—Compound cyme.

*Flower fragrance*.—None.

*Inflorescence*.—Average of 10 days, self-cleaning.

*Inflorescence size*.—2.2 cm in length and 1.8 cm in width.

*Flower type*.—Cyathium, comprised of a linear involucre, a female flower and reduced male flowers, asepalous and apetalous.

*Cyathia quantity*.—Average of 12 per cyme.

*Cyathia aspect*.—Held upwards to outward, mostly drooping.

*Cyathia size*.—An average of 5 mm in depth and 8 mm in diameter.

*Peduncles*.—An average of 7 per cyme, an average of 2 cm in length and 1 mm in width, held in an average angle of 60° (90°=vertical), moderate strength, 143A and 142C, surface is slightly glossy, smooth.

*Pedicels*.—An average of 5 per peduncle, an average of 5 mm in length and 0.5 mm in width, held in an average angle of 60° (90°=vertical), moderate strength, 143A and 142C, surface is slightly glossy, smooth.

*Nectaries*.—3 to 4 per cyathia, flattened, crescent shaped glands each with 2 narrowly acute tips fused into the base of the flower, 1 mm in length and width, 144B in color, surfaces are glabrous and rubbery.

*Floral bracts*.—An average of 8 per cyathia, average of 5 mm in length, 1 mm in width, spatulate to lanceolate in shape, rounded to broadly acute apex, attenuate base, entire margins, both surfaces matte and glabrous, color; upper and lower surface when opening and fully open NN155D.

Reproductive organs (insignificant):

*Gynoecium*.—One pistil; average of 2 mm in length, stigmas; 6-parted, <1 mm in length, 155D in color, style; 0.5 mm in length and 155D in color, ovary; urn-shaped shape, 2 mm in length, 1 mm in diameter, 145C in color.

*Androecium*.—Stamens; an average of 4 reduced stamens, oval in shape and bi-lobed, 0.5 mm in length, 158D in color, hairy surface, no pollen was observed.

*Fruit/seed*.—No fruit or seed has been observed.

It is claimed:

1. A new and distinct cultivar of *Euphorbia* plant named '16EUPD1' as herein illustrated and described.

* * * * *